United States Patent
Tsugawa

(10) Patent No.: US 7,121,281 B2
(45) Date of Patent: Oct. 17, 2006

(54) CONTRACEPTIVE DEVICE WITH WEARING AID

(75) Inventor: Wataru Tsugawa, Tokyo (JP)

(73) Assignee: Shoei Limited Co., Tokyo (JP)

( * ) Notice: Subject to any disclaimer, the term of this patent is extended or adjusted under 35 U.S.C. 154(b) by 77 days.

(21) Appl. No.: 10/959,647

(22) Filed: Oct. 7, 2004

(65) Prior Publication Data
US 2005/0076918 A1     Apr. 14, 2005

(30) Foreign Application Priority Data
Oct. 10, 2003 (JP) .............................. 2003-351838

(51) Int. Cl.
*A61F 6/04* (2006.01)

(52) U.S. Cl. .................. 128/844; 128/842; 128/918; 604/346; 604/347; 604/355

(58) Field of Classification Search ............... 128/844, 128/842, 918; 604/346, 347, 349, 355
See application file for complete search history.

(56) References Cited

U.S. PATENT DOCUMENTS

| | | | |
|---|---|---|---|
| 4,798,600 A | 1/1989 | Meadows | 604/347 |
| 4,934,382 A * | 6/1990 | Barone, Jr. | 128/844 |
| 5,163,448 A | 11/1992 | Foldesy | 158/844 |
| 5,197,957 A * | 3/1993 | Wendler | 604/352 |
| 5,853,006 A | 12/1998 | Metz | 128/844 |

* cited by examiner

*Primary Examiner*—Henry Bennett
*Assistant Examiner*—Camtu Nguyen
(74) *Attorney, Agent, or Firm*—Kubovcik & Kubovcik

(57) ABSTRACT

The present invention provides a condom with a wearing aid comprising a natural or synthetic rubber condom and a wearing aid, wherein, when the outer peripheral wall of the condom is rolled up from the open end of the condom toward the closed end thereof so as to be turned inside, a band-shaped elastic material is stacked on the outer periphery near the open end and rolled up together into the inside of an rolled up part, where the elastic material is selected from (1) a band shaped elastic high polymer material, as Material A provided with a number of cut off aperture parts or a number of cuts almost orthogonal to the longitudinal direction of the band, or (2) an expandable bandage or an band-shaped non-woven stretch fabric as Material B.

3 Claims, 4 Drawing Sheets

CONTRACEPTIVE DEVICE WITH WEARING AID

BACKGROUND OF THE INVENTION

1. Field of the Invention

The present invention relates to a male contraceptive device comprising a condom and a wearing aid that is easily applied.

2. Related Background Art

A so-called condom of a male contraceptive device has a teat integrally formed with a closed end of a tip of the condom, and usually has a ring integrally formed with the open end of a back end. With the ring of this open end as a base, the outer peripheral part of the condom is rolled up toward the closed end so as to be turned inside to form a rolled-up part (as can be seen in FIG. 9), and then, it is packaged, respectively, and commercialized. At the application time, the closed end of the tip, which becomes the inside of the condom, is brought into contact with a tip of penis, and is applied on the penis while unrolling this rolled-up part.

However, since there is a trend that the thinner condom is the more preferred, the rolled-up part based on this ring ends up having a thickness (diameter) of only approximately 3 to 4 mm, which is very small compared to the size of a human finger, and results in the problem that the application is difficult at the application time.

Therefore, various devices have been proposed for eliminating this inconvenience.

For example, a ring to be used at the application time is proposed, in which guide rods having protrusions for preventing falling-off are assembled inside the rubber ring comprising irregularities for identifying the face side of the condom in a form to provide a space in the center for inserting the penis, and the bottom face sheet provided with an insertion port in the center is attached to the bottom of the rubber ring, and the condom is sandwiched up and down by the guide rods and the bottom face sheet. However, though this is relatively simple in the structure, if the rubber ring is prone to excessively deform, there will arise problems, for example, the bottom face sheet may be torn and broken; or such a tool has to be purposely provided for use at the application time; or the ring is easily contaminated by jelly coated on the condom and is difficult to keep clean (for example, see patent document 1).

Further, though disclosures are made for an application tool provided with a base to support the condom in an U-shaped cylinder and a groove to fix the condom as well as an annular condom applicator for holding the condom so as to make the application easy and the like, there are such defects that, after the condom is set once on the application device and the applicator, it is applied on the penis, and yet, it must be removed after the application; or it must be clean by itself as the time as it is contaminated with a coated jelly; or the condom must be purposely applied on the applicator or the like at the application time for use; or the applicator must be ready for use at all the time (for example, see patent document 2, patent document 3 and patent document 4).

Furthermore, a disclosure is made that, to make the application of the condom easy, when the rolled-up part is to be formed by rolling up the condom based on the ring of the open end, in case it is rolled up with at least a piece of tape shaped material or a pair of tape shaped material attached, this tape shaped material may be pulled to the root of the penis at the application time, and therefore the rolled-up part is unrolled to make the application easy.

However, according to this method, though there is an advantage of not using the applicator and other aids purposely, and tape material having smaller width and thickness is preferred, there occur several problems, for example, the difficulty in pulling the tape at the application due to the smaller width and thickness, the difficulty in rolling-up for forming a rolled-up part, or the difficulty in grasping the tape due to sticking thereof to jelly when the jelly is coated on the condom. On the other hand, when the width and/or the thickness of the tape is increased, for example only a part of the rolled-up part becomes bulky and looks bad. Further, although there is the advantage of easy pulling at the application when the both are increased, there occurs the problem that the shape of the rolled-up part is not circular but flat, which looks extremely bad, and in addition, the condom becomes difficult to be applied (for example, see patent document 5, patent document 6, patent document 7, and patent document 8).

Further, a condom formed by a soft film such as a poly vinyl chloride film is proposed. Here, since it is difficult to integrally form a condom with a poly vinyl chloride film, two sheets of the film are seamed by heat-sealing to form a side part of the condom having a shape that is slightly loose compared to the penis in erection. However, as some burrs are produced at the heat-sealed part, the condom must be formed so that the burrs face the penis side. In addition, since this condom is easily fallen off due to the size that is a little loose, to prevent the falling-off, a circular ring of an expandable silicon rubber of 5 mm in diameter that is a little smaller than the open periphery of the film condom is used at the neighbor hood of the root of the penis. However, as the condom is made by seaming two sheets of film by heat-sealing, pin holes are easily formed at the seam part, so that there may be a problem in the effect for contraception. Moreover, as burrs are formed at the seam part, the formed condom must be turned inside out to put the burrs to the inside of the condom. Also, some wrinkles may be formed even though the film is flexible, and the tips of some wrinkles may be hard enough to injure the vaginal wall or to cause pain, which is not always preferable, and a damage to the penis may be caused by the burrs.

Thus, since the condom of the flexible vinyl chloride film is formed a little larger than the penis, there are various problems such as easy formation of the wrinkle across the whole part of the condom and the difficulty in preventing the formation of the pin holes and the like, and such a condom is not practical (for example, see patent document 9).

Further, the present applicant has previously proposed, in the male contraceptive device comprising a condom and a wearing aid, an almost circular ring shaped product in the profile as a wearing aid in which the inner periphery of the ring shaped product is approximately equal to the size of the outer periphery of the condom and, moreover, provided with constrictions at one or more places from the outer periphery toward the inner periphery and/or from the inner periphery toward the outer periphery; or a wearing aid comprising a ring shaped product, of which profile is circular and, moreover, provided with constrictions at one or more places of the ring shaped product; or further, a wearing aid formed in a ring-shape by coil-shaped member. Although the condoms with these wearing aids are easy to produce and have a good advantage of easy application, there arises a problem that since these wearing aids are used as a core part when rolled up from the open end toward the closed end of the condom, the shape of cuts and compressions formed in the wearing aid and the coil-shaped member appears as the shape of the rolled-up part of the condom, and, for example, in the case of the coil-shaped member, the coil appears as a bellows-like rolled-up part, and the shape of the cuts and the compressions also appears in the rolled-up part as it is, and therefore, it looks bad, and in case of applying it on the penis, it feels like gritty, and the application is not always good (for example, see patent document 10, patent document 11 and patent document 12).

[Patent Document 1] Japanese Patent Application Laid-Open No. 10-165433

[Patent Document 2] Japanese Patent Application Laid-Open No. 7-308336

[Patent Document 3] Japanese Patent Application Laid-Open No. 6-14952

[Patent Document 4] Japanese Patent Application Laid-Open No. 6-154260

[Patent Document 5] Japanese Patent Application Laid-Open No. 8-56978

[Patent Document 6] Japanese Patent Application Laid-Open No. 8-252277

[Patent Document 7] Japanese Patent Application Laid-Open No. 6-197921

[Patent Document 8] Japanese Patent Application Laid-Open No. 9-24059

[Patent Document 9] Japanese Patent Application Laid-Open No. 9-47466

[Patent Document 10] Japanese Patent Application Laid-Open No. 2002-264874

[Patent Document 11] Japanese Patent Application Laid-Open No. 2002-306657

[Patent Document 12] Japanese Patent Application Laid-Open No. 2002-306658

As described above, since condoms are small compared to the size of the human hand, and thus conventional condoms are difficult to apply on the penis, various attempts to apply the condoms more easily have been made. However, further improvements of condoms are needed that a feeling of application is good, their production is easy, there is no sense of incompatibility between the product appearance and the application atmosphere, application of a condom on the penis is smooth and easy, the wearing aid can be easily removed after application of the condom and the like.

SUMMARY OF THE INVENTION

The present invention has been made to solve the above described problems and to overcome the problems to be solved.

The present invention relates to a condom with a wearing aid comprising a natural or synthetic rubber condom and a wearing aid, wherein a band of elastic material is stacked and rolled up into a rolled-up part while the band is kept to be adjacent to the outer peripheral surface near the open end, where the band of elastic material is selected from (1) Material A, which is a band-shaped elastic high polymer material provided with a number of cut off aperture parts, or a number of cuts approximately orthogonal to its longitudinal direction, or (2) Material B, which is an stretchable bandage or a band-shaped non-woven fabric of elastic yarn when the outer peripheral wall of the condom is rolled up so as to be turned inside from the open end of the condom toward the closed end.

BRIEF DESCRIPTION OF THE DRAWINGS

FIG. 8A shows a side view of the male contraceptive device in a state prior to forming the rolled-up part; and FIG. 8B shows a side view of the male contraceptive device in the midst state of forming the rolled-up part, and FIG. 8C shows a side view of the male contraceptive device in a state of completing the formation of the rolled-up part.

DESCRIPTION OF THE PREFERRED EMBODIMENTS

Here, as the elastic high polymer material for Material A of the wearing aid, a non-woven fabric having an stretchable property or an stretchable elasticity is cited such as a natural rubber, a butadiene synthetic rubber, a nitrile rubber, a chloroprene synthetic rubber, an isoprene synthetic rubber, a butyl rubber, an ethylene-propylene rubber, an acryl rubber, an ethylene-acryl rubber, a silicon rubber, and a synthetic rubber such as polyurethane elastic body, and furthermore, a foam of these natural rubber and the synthetic rubber and a poly urethane foam.

Figure 5:
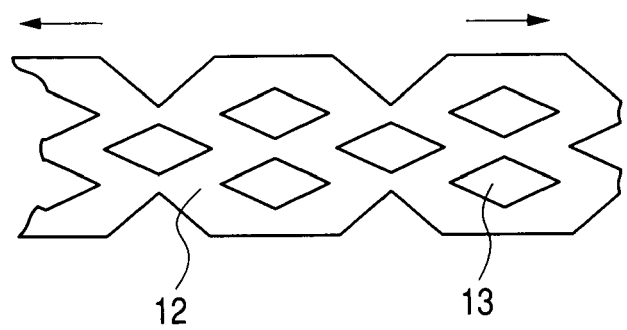
FIG. 5 shows a schematic illustration in case the wearing aid shown in FIG. 4 is expanded in a longitudinal direction.

The band-shaped elastic high polymer material is required to be provided with a number of cut off aperture parts or a number of cuts approximately orthogonal to its longitudinal direction. This is because the elastic high polymer material by itself is too strong in its elasticity, and when it is rolled up into the condom as the wearing aid, there arises a problem that the application is difficult in case of applying it on the penis, and at the same time, it cramps the penis. Hence, as a means to weaken this elasticity, a number of cut off aperture parts are provided in the desired places of the band-shaped material as means to weaken this elasticity or a number of cuts are provided approximately orthogonal to the longitudinal direction of the band. When the cuts or the cut off aperture parts are provided, as shown in FIG. 5, the cuts and cut off aperture parts are widely expanded, and a little force can allow them to expand in the longitudinal direction and the like.

The cut is made from the front surface of the band-shaped elastic high polymer material to penetrate the rear surface, and the length of the cut may be arbitrary. However, the length varies depending on the width of the band-shaped material.

The cut off aperture part is a cut off aperture part provided to penetrate the rear surface from the front surface of the band-shaped material in place of the cut, and may be of an arbitrary shape. For example, such shapes as circle, ellipse, square, rectangle, trapezoid, parallelogram, diamond and the like can be cited, among which circle, ellipse and diamond are preferable.

As the width of the band-shaped elastic high polymer material, though it depends on the thickness of the material, it is about 1 to 5 cm, preferably an approximate 2 cm. The band-shaped material may be constituted such that both ends thereof are coupled or integrated to become ring shaped or turned into a free end. It is preferable that the length of the material is approximately the same as the length of the outer peripheral part of the condom, and even if the length is a little longer or a little shorter, it is alright if the material can be rolled up when the rolled-up part of the condom is formed.

The stretchable bandage or band-shaped non-woven stretch fabric for Material B, may be at least stretchable in the longitudinal direction of the band. Typically, the stretchable bandage is often knitted with polyurethane elastic yarns, but it may be comprised of a knitted fabric such as an stretchable plain stitch. The band-shaped non-woven stretch fabric includes a non-woven fabric adhered to the polyurethane elastic yarns by a bonding agent, a spun bonded non-woven stretch fabric of polyurethane elastomer or a non-woven fabric produced by any one of other materials.

As the width of the stretchable bandage or the band-shaped non-woven stretch fabric, though it depends on the thickness of the material, it is about 1 to 5 cm or preferably approximately 2 cm. The bad-shaped material may be constituted such that both ends thereof are coupled or integrated to form a ring or remain as free ends. It is preferable that the length of the material is approximately the same as the length of the outer peripheral part of the condom, and even if the length is a little longer or shorter, it is appropriate if the material can be rolled up in the rolled-up part of the condom when it is formed.

Figure 8A:
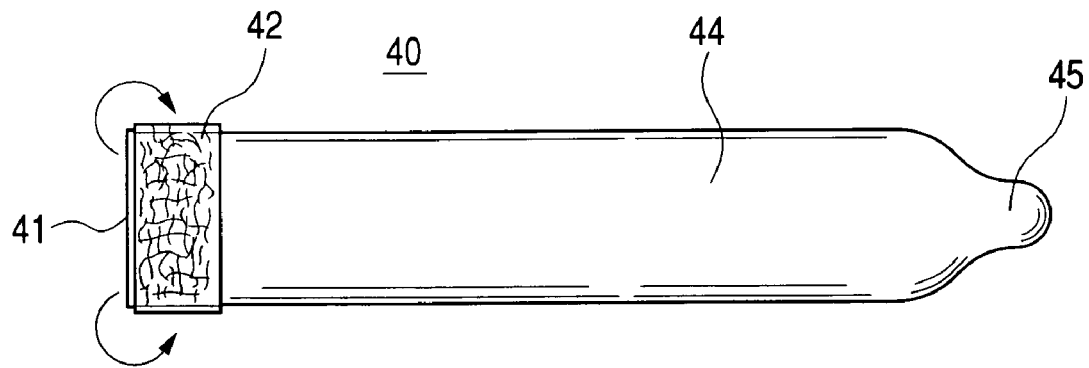
FIGS. 8A, 8B and 8C show a process drawing for producing the wearing aid of the present invention by rolling up it into a condom.
Figure 8B:
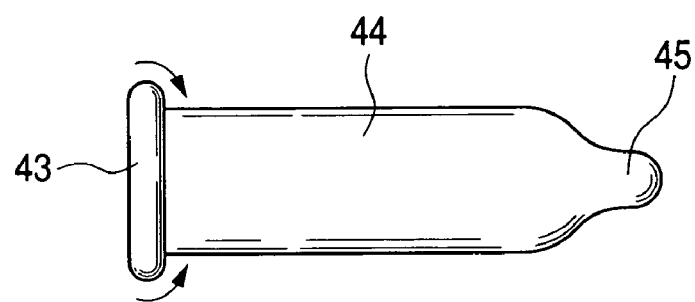
Figure 8C:
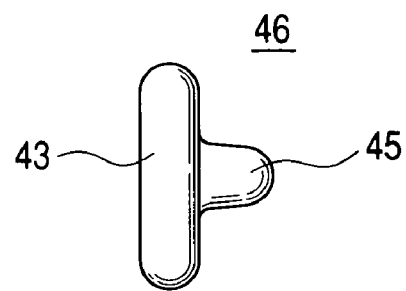

Further, to produce the condom with the wearing aid of the present invention, as shown in FIGS. 8A to 8C, the condom and the wearing aid are put together in a state of the wearing aid adjacent to the outer peripheral surface near the open end of the condom, and the condom is rolled up so that the outer peripheral surface of the condom turns inside, thereby forming the rolled-up part to produce the condom.

The condom used in the present invention can be made from various types of material, which have been widely known. A condom formed of natural or synthetic rubber is most preferable.

The condom may be colored with a coloring agent or formed using other suitable additives. Further, the condom may be coated with the jelly.

The wearing aid may not be colored. However, it may be necessary to device a color that can easily distinguish the wearing aid, preferably considering the combination with the color of the condom. It is preferable to color it as appropriate considering the color that is reasonably compatible with the color of the condom.

As described above, the present invention is a condom with a wearing aid comprising a condom and a wearing aid. The rolled-up part of this condom becomes larger according to the amount of the wearing aid rolled up together, increasing the diameter or the thickness of the rolled-up part. Therefore, though depending on the amount of the wearing aid, the typical diameter or thickness thereof is increased from about 3 to 4 mm to about 5 to 8 mm or more, so that the size, which is small compared to the human hand, becomes larger correspondingly. This makes the application easy, and allows it to be nice to look at, and has the advantages of an extremely improved feeling of application and easiness of removal after the application.

Furthermore, compared to the conventional wearing aid (the wearing aid, which is a ring object approximately circular in the profile, and in which the inner periphery of the ring object is approximately equal to the size of the outer periphery of the condom, and which is provided with cuts in one or more places from the outer periphery toward the inner periphery and/or from the inner periphery toward the outer periphery; or the wearing aid, which comprises the ring object, and of which profile is circular, and which is provided with constrictions in one or more places of the ring object; or the wearing aid formed in a ring shape by the coil-shaped member), the shape of the rolled-up part becomes smooth without the coil shape used in the core of the rolled-up part emerging as a serpentine rolled-up part or the cut and compression having its shape appeared as it is on the rolled-up part, and furthermore, though the pinholes are prone to arise in the condom by the ring end, no such phenomenon develops in the ring object, and when applying the condom, it does not feel like gritty, thereby improving a feeling of application. A wearing aid formed of bandage or non-woven fabric feels extremely light or soft, thereby improving the sense of application of the condom. In a wearing aid formed of the elastic high polymer material, the shapes of the cuts or cut off aperture parts hardly appear or do not appear at all through the rolled-up part, thus not making it feel gritty. The wearing aid is more expandable than the conventional wearing aids, feels softer, thereby advantageously providing an improved application of the condom.

In addition, since the size (diameter) of the rolled-up part of the condom becomes large by using the wearing the wearing aid, the application in the middle of the sex acts is extremely easy, and cleaning up after the sex acts is extremely simple. Further, since almost every application is made in the midst of the sex acts, interposition of a ribbon-shaped product seems in no way compatible with the atmosphere, and causes a feeling of strangeness. In the case of the wearing aid of the present invention, however, since it does not meet the eye until immediately before the final step of the application, it can be installed just with the sense of conventional condom. Moreover, the wearing aid is simple in structure and easy to produce, and though the rolled-up part is formed by using this aid device, a conventional machine can be used as it is, and further, there is another advantage that when it is packaged as commercial product, it consumes the packing material in almost the same amount as conventional wearing aids.

Furthermore, different from the wearing aid using the tape shaped material, it has an important advantage that it looks good so as to cause no feeling of strangeness, and the shape of the rolled-up part is circular or almost circular for easy application. Particularly, it is said that the application of the condom before starting the sex acts is not common, and the condom is commonly applied during the sex acts. In such a case, the surface of the penis is lubricated by the secretion from the vagina or the like, and so the application is very difficult. The condom of the present invention provides the advantage of easy application even in such a case. Moreover, it provides the advantages also in the production that the structure is very simple; its production is easy; and the conventional machines for producing condoms can be applied without any modification.

The present invention will be specifically described with reference to the drawings.

Figure 9:
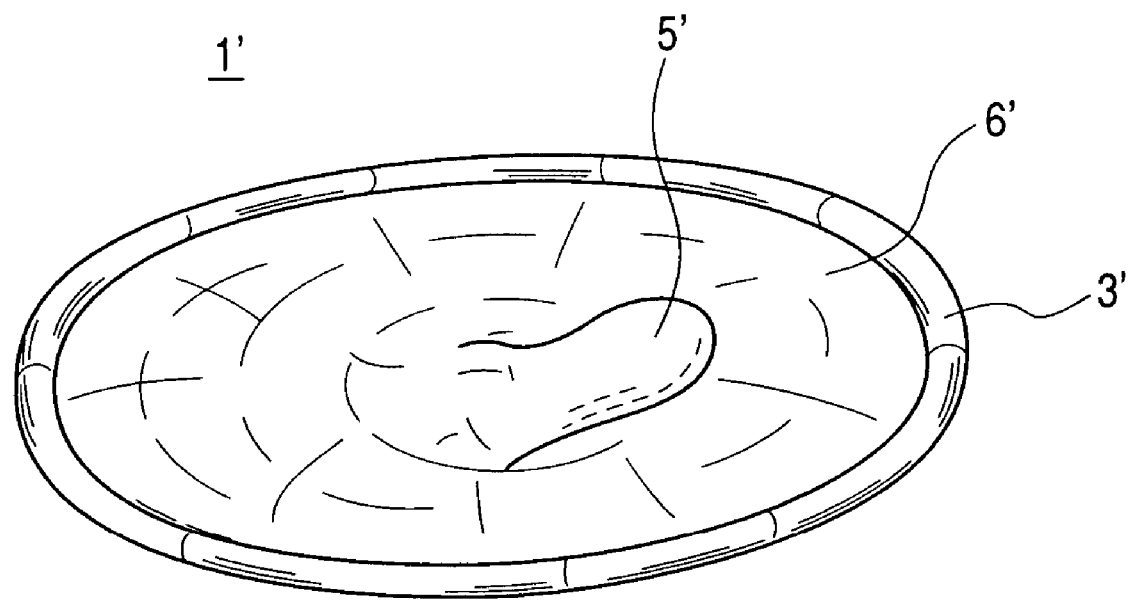
FIG. 9 shows an oblique view of the condom formed with a conventional rolled-up part.

FIG. 9 shows a conventional condom 1', which has usually a ring (not shown) integrally formed with an main condom body at an open end, and based on this ring, a rolled-up part 3' is formed by rolling up the outer periphery of the condom in such a way to be rolled up into the inside till a closed end 6', and the condom 1' rolled up into such a shape is packaged, respectively, and it is commercialized.

In this case, the diameter or the size of the ring is slightly larger than the film thickness of the condom, and the condom is rolled up with this as a core. However, though the diameter of this ring is slightly larger than the film thickness of the condom, if this film thickness is thick, a sexual feeling is reduced, so that a much thinner type is preferred. Thus, the diameter of the ring has no other choice but to be small. Then, since the size (diameter) of the rolled-up part 3' ends up becoming small, there arises a practical problem in that the unrolling is not easy while an attempt is made to unroll and apply the condom on the penis.

Note that reference numeral 5' in FIG. 9 denotes a teat.

Figure 1:
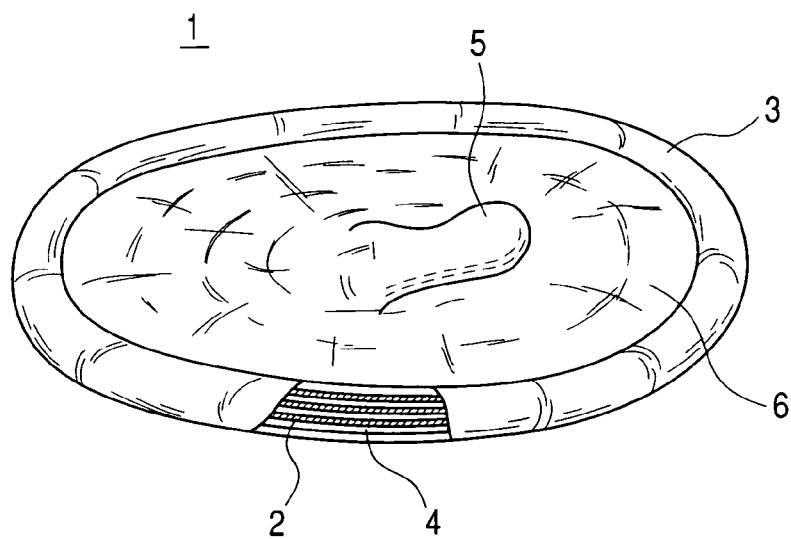
FIG. 1 is an oblique view of a male contraceptive device of the present invention in which a rolled-up part is partially cut away.

The condom with the wearing aid of the present invention is shown in FIG. 1. FIG. 1 is an oblique view of the condom with the wearing aid in which a part of the rolled-up part is cut away. Here, reference numeral 2 denotes a wearing aid, reference numeral 3 a rolled-up part, reference numeral 4 a main condom body, reference numeral 6 a closed end, and reference numeral 5 a teat, respectively.

The condom 1 with the wearing aid shown in FIG. 1 of the present invention, when forming the rolled-up part 3 by using the wearing aid 2, is rolled up as shown in FIGS. 8A to 8C, in such a way that both the condom and the wearing aid come into the inside of the outer periphery of the condom in a state of the wearing aid abutted against the outer peripheral surface near the open end of the condom, thereby forming the rolled-up part. By so doing, the wearing aid is intervened in the rolled-up part of the condom, and regardless of the film thickness of the condom, the size (diameter) of the rolled-up part 3 can be adjusted to a size easy to be applied.

Figure 2:
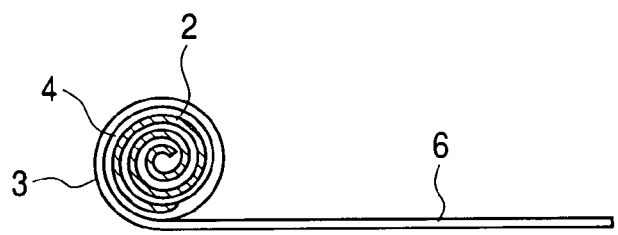
FIG. 2 is a sectional view of a part of the rolled-up part of the male contraceptive device of FIG. 1.

FIG. 2 shows a sectional view of a part near the rolled-up part 3 in FIG. 1, wherein reference numeral 2 denotes a wearing aid, reference numeral 3 a rolled-up part, reference numeral 4 a main condom body, and reference numeral 6 a closed end, respectively. The rolled-up part 3, as can be seen in FIGS. 8A to 8C, is formed in such a way that the band-shaped wearing aid is rolled up and the condom is rolled up in a state of the wearing aid adjacent to the outer peripheral surface near the open end of the condom. In this way, since the band-shaped elastic material and the main condom body are alternately rolled up into a sandwiched shape from the open end of the condom toward the closed end to constitute a rolled-up part, the size of the rolled-up part becomes large to make the application easy, and because of the band-shaped shape, the unrolling of the rolled-up part becomes smooth in case of applying, and this gives a smooth feeling of application and makes the rolled-up part easy to handle.

Figure 3:
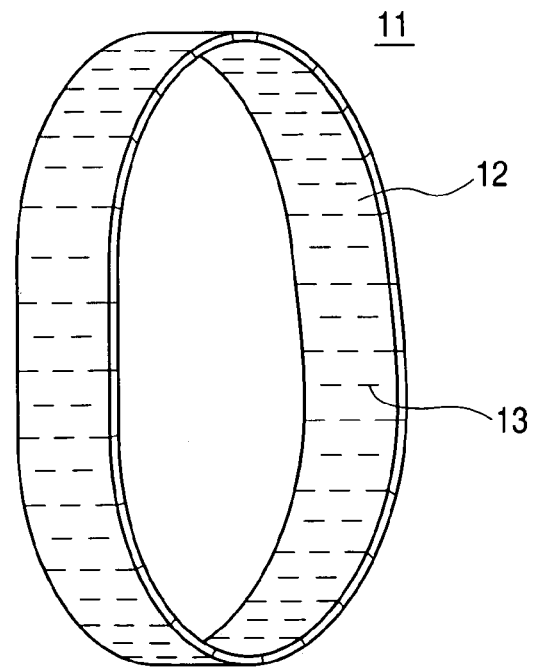
FIG. 3 shows an oblique view of a wearing aid.

FIG. 3 shows a rubber band shaped wearing aid 11, in which a number of cuts 13 are provided orthogonal to the longitudinal direction of an elastic material 12.

Figure 4:
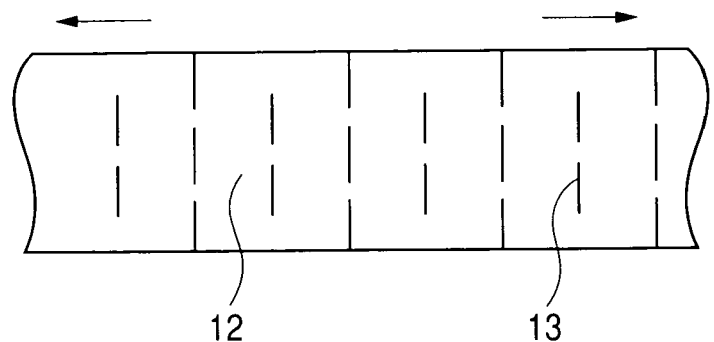
FIG. 4 shows a partially enlarged front view of the wearing aid shown in FIG. 3.

FIG. 4 is a partially enlarged view in which the cut 13 is provided in the longitudinal direction of the elastic material 12 shown in FIG. 3. In FIG. 4, if the elastic material 12 is expanded like an arrow mark of the longitudinal direction, it takes a shape of the state shown in FIG. 5. However, in FIG. 5, the expanded material is schematically shown. In case the cut is made in this way so that the expansion is made in the longitudinal direction, that is, in case the size of the rubber band shaped wearing aid is expanded, the wearing aid can be expanded by a little force compared to the case where there is no cut provided, and can be removed after the application of the condom on the penis. Further, by providing such a cut, the elastic material can be easily expanded. Further, even if the rolled-up part of the condom is formed by using this wearing aid, there will appear almost no shape of the cut in the rolled-up part.

Figure 6:
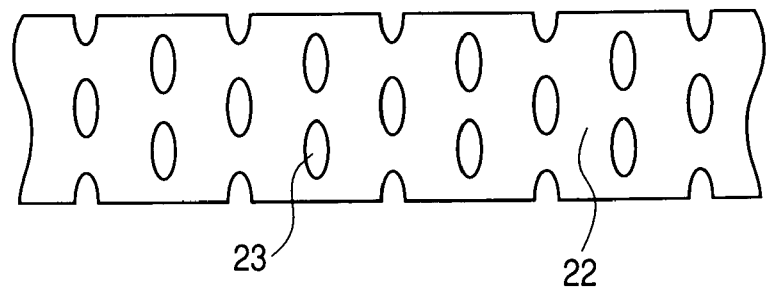
FIG. 6 shows a partially expanded view showing another example of the wearing aid.

FIG. 6 shows a partially enlarged view showing another example of the wearing aid, where there is provided a number of elliptical cut off aperture parts 23 in the longitudinal direction of the elastic material 22. In case the aperture part is provided in this way so that it expands in the longitudinal direction, the wearing aid can be expanded by a little force and can be removed after the condom is applied on the penis compared to the case where there is no aperture part provided, and can be removed after the application of the condom on the penis. Further, by providing such a aperture part, the elastic material can be easily expanded. Further, even if the rolled-up part of the condom is formed by using this wearing aid, there will appear almost no shape of the indentation of the aperture part and the like in the rolled-up part.

Figure 7:
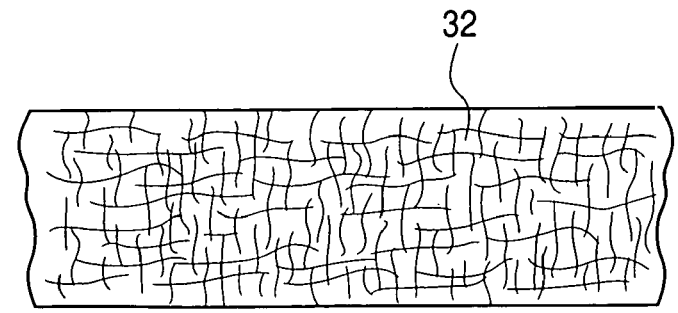
FIG. 7 shows a partially expanded view showing another example of the wearing aid.

FIG. 7 shows a partially enlarged view showing another example of the wearing aid, which is constituted here by an expandable bandage 32 or an band-shaped non-woven stretch fabric 32. In the case of the wearing aid of the bandage or the non-woven fabric, there is an extremely light feeling or no gritty feeling, and the expandability is good compared to the conventional wearing aid, and a feeling of application is favorable as it feels soft, and the like.

FIGS. 8A to 8C show a process drawing in case of producing the condom with the wearing aid by rolling up the wearing aid into the condom.

FIG. 8A shows a condom 40 before forming a rolled-up part 43. Here, reference numeral 44 denotes a main condom body, reference numeral 42 a wearing aid comprising an expandable bandage or a band-shaped expandable non-woven fabric, reference numeral 45 a teat, and reference numeral 41 a ring formed integrally with the main condom body 44 in the open end of the condom.

In FIG. 8A, as shown by an arrow mark from the open end side, when the condom and the wearing aid are rolled up to form the rolled-up part 43, an intermediate process part as shown in FIG. 8B is formed.

When the condom is further rolled up, a condom 46 with a wearing aid in a shape of rolling up the wearing aid as shown in FIG. 8C into the rolled-up part is formed.

What is claimed is:

1. A condom with a wearing aid comprising a condom of a natural rubber or a synthetic rubber and a wearing aid comprising an elastic high polymer material in the form of a band, wherein, when the outer peripheral wall of the condom is rolled up from the open end of the condom toward the closed end thereof so that said outer peripheral wall is turned inside, the band is stacked on the outer peripheral surface near the open end and rolled up together so as to be rolled up into the inside of the rolled-up part, the band being provided with either a number of cut off aperture parts or a number of cuts almost orthogonal to the longitudinal direction of the band.

2. The condom with the wearing aid according to claim 1, wherein the elastic material is selected from the group consisting of a natural rubber, a synthetic rubber, a natural rubber foam, a synthetic rubber form or a polyurethane form.

3. A condom with a wearing aid comprising a condom of a natural rubber or a synthetic rubber and a wearing aid comprising an elastic high polymer material in the form of a band, wherein, when the outer peripheral wall of the condom is rolled up from the open end of the condom toward the closed end thereof so that said outer peripheral wall is turned inside, the band is stacked on the outer peripheral surface near the open end and rolled up together so as to be rolled up into the inside of the rolled-up part, the band being provided with a number of cut off aperture parts, where the shape of the cut off aperture parts is selected from a circle, an ellipse or a diamond.

* * * * *